(12) United States Patent
Volker

(10) Patent No.: US 7,562,577 B2
(45) Date of Patent: Jul. 21, 2009

(54) ACOUSTIC TESTING APPARATUS FOR TESTING A LAMINATE MATERIAL AND AN ACOUSTIC TESTING METHOD FOR TESTING A LAMINATE MATERIAL

(75) Inventor: Arno Willem F. Volker, Delft (NL)

(73) Assignee: Nederlandse Organisatie Voor Toegepast-Natuurwetenschappelijk Onderzoek TNO, Schoemakerstraat 97, Delft (NL)

( * ) Notice: Subject to any disclaimer, the term of this patent is extended or adjusted under 35 U.S.C. 154(b) by 180 days.

(21) Appl. No.: 10/571,736

(22) PCT Filed: Sep. 15, 2004

(86) PCT No.: PCT/NL2004/000640

§ 371 (c)(1),
(2), (4) Date: Jan. 8, 2007

(87) PCT Pub. No.: WO2005/026716

PCT Pub. Date: Mar. 24, 2005

(65) Prior Publication Data

US 2007/0199381 A1  Aug. 30, 2007

(30) Foreign Application Priority Data

Sep. 16, 2003  (EP) .................................. 03077925

(51) Int. Cl.
*G01N 24/00* (2006.01)
(52) U.S. Cl. .............................. 73/625; 73/597; 73/602; 73/628
(58) Field of Classification Search .................... 73/625, 73/628, 597, 602
See application file for complete search history.

(56) References Cited

U.S. PATENT DOCUMENTS 3,858,437 A * 1/1975 Jarznski et al. ............... 73/597

(Continued)

FOREIGN PATENT DOCUMENTS

| EP | 0 515 734 | 12/1992 |
| EP | 0 829 714 | 3/1998 |
| EP | 0 878 691 A1 | 11/1998 |

OTHER PUBLICATIONS

Shevaldykin V.G.; "Thickness Measurement of Objects Having Variable Sound Velocity With Depth Without a Standard"; Soviet Journal of Nondestructive Testing, Consultants Burea, New York, US, vol. 3, No. 22, Mar. 1, 1986, pp. 157-160, XP002075762.

*Primary Examiner*—Hezron Williams
*Assistant Examiner*—J M Saint Surin
(74) *Attorney, Agent, or Firm*—Bruce S. Londa; Norris McLaughlin & Marcus, PA

(57) ABSTRACT

An acoustic testing apparatus for testing a laminate material comprising at least one layer of a first material having a first velocity for a first vibration mode and at least one layer, adjacent to said first layer, of a second material having a velocity for a second vibration mode, approximately equal to said first velocity, said acoustic testing apparatus comprising: a first transducer for projecting an acoustic test signal onto a first layer of said at least one layer of a first material disposed in a testing zone, wherein a second transducer for receiving said test signal from said testing zone, and in that said first transducer is adapted to project said test signal at an angle so as to generate in said first layer vibrations of at least said first vibration mode, wherein said vibrations of said first vibration mode are incident on an interface with said layer of said second material under an incidence angle so as to produce in said second layer vibrations of at least said second vibration mode, so that refraction of said test signal at said interface is suppressed.

15 Claims, 3 Drawing Sheets

U.S. PATENT DOCUMENTS

| | | | |
|---|---|---|---|
| 4,892,701 A * | 1/1990 | Mauvieux et al. | 376/258 |
| 5,737,153 A * | 4/1998 | Gavit | 360/261.2 |
| 6,572,548 B2 * | 6/2003 | Cerofolini | 600/443 |
| 7,207,940 B2 * | 4/2007 | Satoh | 600/437 |
| 2003/0079545 A1 | 5/2003 | Pop et al. | 73/627 |

* cited by examiner

ACOUSTIC TESTING APPARATUS FOR TESTING A LAMINATE MATERIAL AND AN ACOUSTIC TESTING METHOD FOR TESTING A LAMINATE MATERIAL

TECHNICAL FIELD

The invention relates to an acoustic testing apparatus for testing a laminate material and an acoustic testing method for testing a laminate material.

BACKGROUND TO THE INVENTION AND PRIOR ART

Acoustic testing is a technique which uses sound waves to test an object. Ultrasonic non-destructive testing is one such technique, which has found application in the testing of laminate materials, such as metal laminate systems used in the aerospace industry. Conventional non-destructive testing methods for laminates are based on transmission measurements or very low frequency reflection measurements. These techniques lack the capability of providing information about the depth of defects in the material. In conventional reflection techniques a single transmitter/receiver transducer is arranged to project an acoustic test signal which is incident on the test material at approximately zero degrees (it should be noted that incidence angles are measured with respect to a normal which is at 90 degrees to the surface of the test material). The waves reflected by the test material are then received by the same single transducer. Although some reflection techniques provide some information about the depth of defects, it has been found that, due to the fine layering of laminate materials, the detected reflection images are often very complicated and difficult to process due to the vast number of reflections. Thus, reflection testing techniques have not been considered as a viable option for testing laminate materials.

It is an object of the present invention to address those problems encountered in conventional acoustic testing apparatuses for testing laminate materials. In particular, it is an object to provide a testing apparatus and method which identifies the depth of defects detected in the laminate without requiring complex signal processing.

SUMMARY OF THE INVENTION

According to a first aspect of the invention, there is provided an acoustic testing apparatus for testing a laminate material comprising at least one layer of a first material having a first velocity for a first vibration mode and at least one layer, adjacent to said first layer, of a second material having a velocity for a second vibration mode, approximately equal to said first velocity, said acoustic testing apparatus comprising:

a first transducer for projecting an acoustic test signal onto a first layer of said at least one layer of a first material disposed in a testing zone, characterised by:

a second transducer for receiving said test signal from said testing zone, and in that said first transducer is adapted to project said test signal at an angle so as to generate in said first layer vibrations of at least said first vibration mode, wherein said vibrations of said first vibration mode are incident on an interface with said layer of said second material under an incidence angle so as to produce in said second layer vibrations of at least said second vibration mode, so that refraction of said test signal at said interface is suppressed.

The inventors have found that for most laminate materials, the shear wave (S-wave) velocity in the material of one layer is approximately the same as the compression wave (P-wave) velocity in the material of its surrounding layers. Consequently, if an S-wave is projected under a given (non-0 degree) angle into a layer of the first material, the S-wave is converted into a P-wave travelling into the second layer at the interface with a layer of the second material from the interface, travelling at the same angle corresponding to the angle of incidence. Consequently, there is no refraction at the interface, but there are reflections at every boundary between adjacent layers. Because no refraction occurs at the boundary between adjacent layer, the laminate material appears homogenous to the receiver, thus interpretation of the reflected test signal is greatly simplified. The present invention is based on the insight that the material properties, in particular, the elastic properties, of the laminate material can be exploited to project a test signal which when reflected by the laminate material comprises data where the structural features are directly visible in the collected data.

In such a way, it becomes possible to identify the depth of defects in the laminate, which enables a more accurate test result to be achieved. Furthermore, high structural detail is obtainable, which can be used to give a structural interpretation of a laminate, which enables a complex structure and any defects to be seen directly. For example, if a plurality of defects is detected, yet it is found that they are distributed over a plurality of layers in the laminate, the safety implications are less serious than for a plurality of defects found in the same layer, as these may lead to a crack or other serious damage occurring in the laminate. In contrast to conventional testing methods, the present invention allows the depth of each defect to be identified.

Because the laminate material appears substantially homogeneous to the receiver, the interfaces between, the analysis of data received by the second transducer is simplified, in addition structural features are directly derivable from the data acquired by the second transducer.

These advantages result in a more accurate testing of the laminate allowing a more accurate image of the tested laminate material to be produced without reflections caused by refraction of the test signal having to be processed.

In a preferred embodiment, said first transducer is adapted to project said test signal at an angle so that said vibrations of said first vibration mode predominate in said first layer. Because vibrations of the first vibration mode predominate in the first layer, signal processing requirements due to components in said received signal corresponding to other vibrations generated in the first layer are reduced.

In a preferred embodiment, said second transducer is adapted to receive a reflected test signal at least one location. By receiving the reflected signal at a plurality of locations a more detail of the structural features of the laminate material are obtained, since defects cause the test signal to be reflected over a variety of angles depending on the structural features of the defect. In particular, deeper reflections will be recorded at larger offsets.

In a preferred embodiment, data associated with said laminate material is directly derivable as a function of time and position from said reflected test signal received by said second transducer. Because data associated with the laminate material is directly derivable as a function of time and position from the reflected test signal assessment of the laminate material can take place quickly without requiring large processing resources. In particular, time to depth conversion is very simple, that is by multiplication by a scalar.

In a preferred embodiment, the angle corresponds to the angle of incidence of said test signal on said first layer measured with respect to the normal, and is between approximately 14 and 30 degrees. It has been found that such an angle range in certain laminate materials produces an optimum generation of S waves whilst suppressing the generation of P waves in the first layer of the laminate material on which the test signal is incident.

In a preferred embodiment, the frequency of said test signal is in excess of the order of 20 MHz. It has been found that depending on the dimensions of the layers of the laminate material, such a frequency range allows the most detailed analysis of structural features to take place.

In a preferred embodiment, a plurality of second transducers arranged in an array. By providing an array of second transducers reflection data may be received from a plurality of locations simultaneously. Thus, increasing the speed and accuracy of data acquisition.

In a further embodiment, said second transducer/s is/are arranged to be moveable to a plurality of locations for receiving said reflected test signal. Thus, further increasing amount of data that may be acquired by the second transducer/s.

According to a second aspect of the invention, there is provided an acoustic testing method for testing a laminate material comprising at least one layer of a first material having a first velocity for a first vibration mode and at least one layer, adjacent to said first layer, of a second material having a velocity for a second vibration mode, approximately equal to said first velocity, said acoustic testing method including the steps of: using a first transducer to project an acoustic test signal onto a first layer of said at least one layer of a first material disposed in a testing zone, characterised by:

using a second transducer to receive said test signal reflected from said testing zone, and by adapting said first transducer to project said test signal at an angle so as to generate in said first layer vibrations of at least said first vibration mode, wherein said vibrations of said first vibration mode are incident on an interface with said layer of said second material under an incidence angle so as to produce in said second layer vibrations of at least said second vibration mode, so that refraction of said test signal at said interface is suppressed. acoustic testing apparatus for testing a laminate material comprising at least one layer of a first material having a first velocity for a first vibration mode and at least one layer, adjacent to said first layer, of a second material having a velocity for a second vibration mode, approximately equal to said first velocity, said acoustic testing apparatus comprising:

a first transducer for projecting an acoustic test signal onto a first layer of said at least one layer of a first material disposed in a testing zone, characterised by:

a second transducer for receiving said test signal reflected from said testing zone, and in that said first transducer is adapted to project said test signal at an angle so as to generate in said first layer vibrations of at least said first vibration mode, wherein said vibrations of said first vibration mode are incident on an interface with said layer of said second material under an incidence angle so as to produce in said second layer vibrations of at least said second vibration mode, so that refraction of said test signal at said interface is suppressed.

BRIEF DESCRIPTION OF THE DRAWINGS

In order that the invention may be more fully understood embodiments thereof with now be described by way of example only, with reference to the figures in which.

DESCRIPTION OF THE PREFERRED EMBODIMENTS

Figure 1:
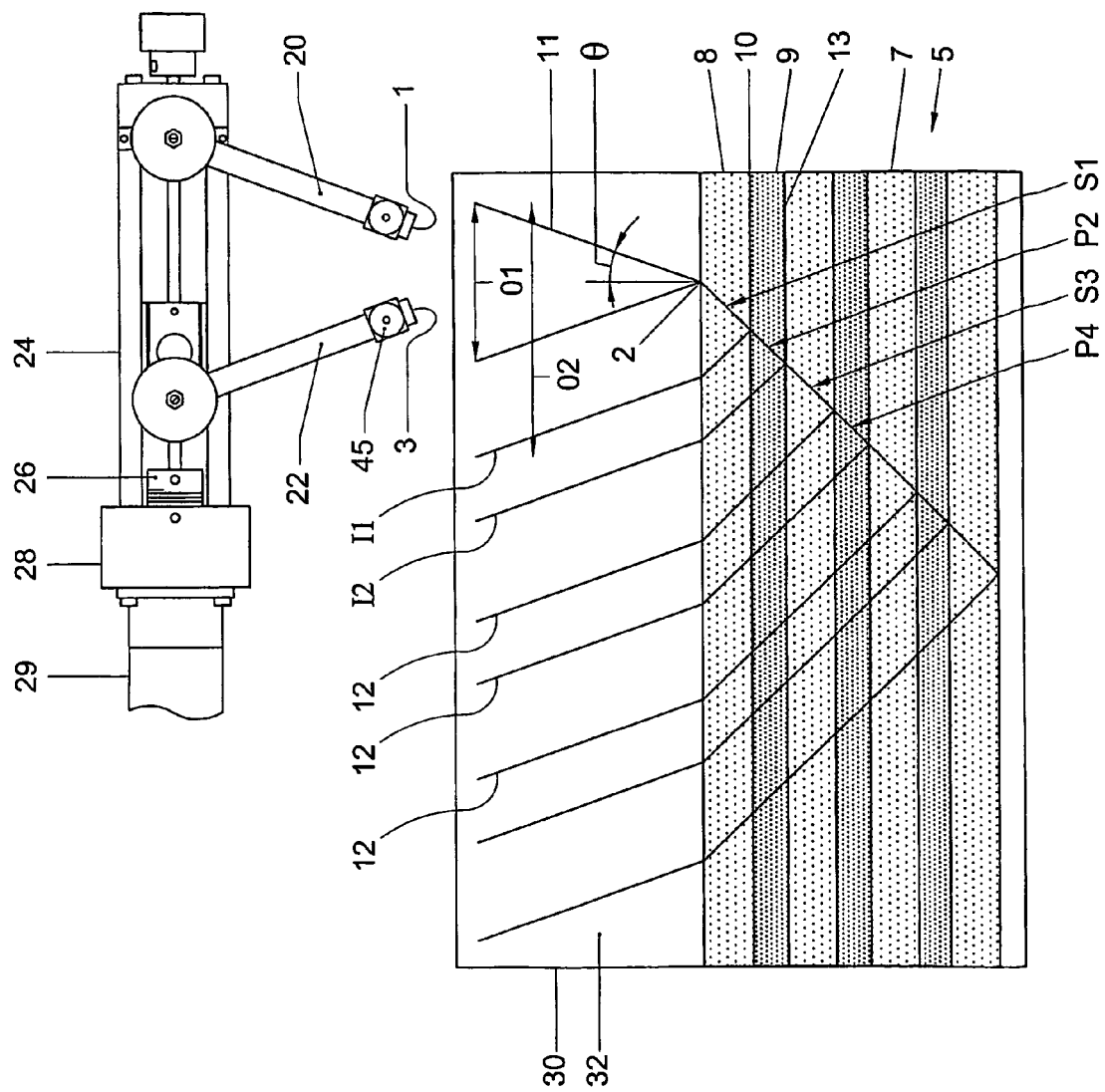
FIG. 1 shows diagrammatically an acoustic testing apparatus according to an embodiment of the present invention.

The acoustic testing apparatus shown in FIG. 1 comprises a source 1, typically including a first transducer, for projecting a test signal 11 onto a laminate material 7 in a test zone 5. Also provided is a receiver 3, typically including a second transducer, for receiving a test signal 12 having passed through the test zone 5. The receiver 3 is arranged to be disposed at least one location O1, O2, etc. Alternatively, a plurality of receivers may be disposed in an array in an acquisition plane. The test signal is incident on a surface of the laminate material 7 at least one location 2. For each location 2 several measurements are taken with varying distance O1, O2, etc, also referred to as offset, between the source 1 and the receiver 3. This provides an optimum depth resolution of the image. The laminate material 7 comprises a plurality of layers 8, 9. At the interface 10 between adjacent layers 8, 9 reflections of the test signal occur. Reflections from deeper layers occur at higher offsets, that are at greater distance from the source, at the acquisition plane in which the receiver 3 is disposed. After completion of the offset scan, a measurement is taken at a next location. In this way an entire image can be obtained. According to an embodiment of the present invention, offsets O1, O2, etc are combined to increase the depth range of the testing measurement.

Although the embodiment shown in FIG. 1 depicts a reflective testing apparatus, that is one where the test signal is reflected from the test laminate material, the invention is not limited in this respect, and may be applied to a transmissive testing apparatus, that is in an apparatus in which the source and receiver are disposed on opposite sides of the laminate material.

The source produces a sound wave. The sound wave may be a transmitted vibration of any frequency. The sound wave generated may comprise components having a first vibration mode and/or a second vibration mode. Typical vibration modes include shear wave components (S-wave) and compression wave components (P-wave). The invention has particular application in ultrasound testing, however, the invention is not limited in respect of the frequency of the sound wave produced by the source. Typically, the frequency is of the order of 20 Mega-Hertz. The source may comprise any source suitable for generating a sound wave, for example, a piezoelectric source including a purely ceramic or a composite source. Alternatively, the sound wave may be generated by laser excitation. In contrast to conventional sources, which generate a test signal having frequency of typically 10 MHz or lower, the source according to an embodiment of the present invention, preferably generates a test signal having a higher frequency. In addition to conventional excitation techniques, and in contrast to conventional test signals, the test signal is preferably generated using "Sweep" technology, as is for example, described in "Evaluation of seismic resolution in experimental facility data; Design and optimization of source signals", Mattieu Ter Morshuizen, 1997, M.Sc. Thesis, Delft University of Technology. Although, the "Sweep" technique is known, it has not previously been used in acoustic testing apparatuses. The inventor has identified this particular new and advantageous application of "Optimized Sweep" technology.

"Optimized Sweep" technology produces a test signal having a high resolution, since the transfer function of the transducer is corrected for to produce a sharp pulse in the time domain. It has been found that this technique produces high bandwidth signals (having a large frequency range), having a very short duration in the time domain with a high amplitude peak. Using the "sweep" technique, higher bandwidth signals are achieved by inputting more energy into those frequency components which are weakly emitted by the transducer.

In a particular embodiment, the time resolution of the test signal generated so that it provides a spatial resolution higher than the layer thickness of a typical laminate material to be tested. Thus, the smallest detail in the time direction can be resolved using test signals generated, for example, using the "Sweep" technique. The wavelength of the test signal in the embodiment shown in FIG. 1 is typically in the region of 150 micrometres. However, as set out, the wavelength will depend on the particular laminate to be tested. The bandwidth of the signals is typically greater than 100%. The bandwidth is calculated using the following equation:

bandwidth=(highest frequency component−lowest frequency component/central frequency component)×100%.

This is in contrast to signals using other conventional methods of generation, which typically have a bandwidth of 60%.

Although the present invention has particular application to the testing of metal laminate systems, such as Glare (registered trade mark), the invention is not limited in respect of the laminate material to be tested. However, it will be understood that depending on the laminate material to be tested, the source will be adapted to generate an appropriate test signal, since the test signal will vary depending on the particular material to be tested, since the velocity of waves travelling through the laminate depends on factors such as the density, the Poisson ratios and the Young's modulus of the materials making up the laminate material.

In the embodiment shown in FIG. 1, the laminate material 7 to be tested is Glare (registered trade mark) which is a metal laminate system comprising alternate aluminium 8 and glass fibre reinforced epoxy layers 9. Other laminate materials typically include other metal laminate systems and epoxy containing laminates, including carbon fibre reinforced epoxy and filled epoxy systems. As well as epoxy, the present invention has application to polyurethane containing laminates, where the polyurethane may or may not be reinforced with other materials such as fibres or powdered materials. In certain laminate materials, such as Glare, the layers include alternate metal and epoxy (or other polymer) layers. However, the invention is not limited in this respect, and it is envisaged that the present invention may also be used to test laminates having an epoxy layer including a certain additive adjacent a second non-metal layer or laminate materials comprising a first epoxy based layer including a first additive and a second epoxy based layer having a different additive. In those laminate materials comprising a metal and a non-metal layer, the metal may be selected from group III elements, such as aluminium or titanium, or may also be selected from other metals such as steel, including stainless steel. In particular, however, the choice of the metal is not limited provided the velocity of propagation of S waves in the metal layer is approximately of the same order of magnitude as the propagation velocity of P waves in the non-metal layer.

In the particular embodiment shown, the Glare laminate includes aluminium layers 8 having a thickness of between 300-500 micrometres, typically, approximately 400 micrometres alternating with glass fibre reinforced epoxy layers 9 having a thickness of typically 250 micrometres.

The receiver 3 also typically includes a transducer. The transducer for the receiver may include any one of the same transducers used for the source. Additionally, it has been found that a piezoelectric plastic material, such as polyvinyl difluoride (PVDF) foil transducer may be used, since it functions as a very sensitive receiver.

In the embodiment shown, the test signal 11 is incident on the surface of the laminate at an angle theta of about 20 degrees. When the acoustic test signal is impinges on the surface both pressure (P) and shear (S) waves are generated in the first layer of the laminate material onto which the test signal is projected by the source. The angle theta is determined in accordance with Snell's law and will vary depending on the particular material of the surface of the laminate and the material of the medium directly above the surface. Preferably, the medium directly above the surface is a coupling material, whose properties are chosen so as to effectively couple the energy of the test signal into the test laminate. A coupling apparatus 30, 32 is preferably provided, typically including a container 30 and a coupling medium 32. Typically, the coupling medium is water, as it has been found that water effectively couples the test signal into the laminate material. Alternatively, a plastic wedge disposed on the surface of the laminate also provides a coupling function. It has been found that for a laminate material 7 having an upper surface first layer of aluminium in contact with water as the coupling medium, the angle theta is preferably between 14 and 30 degrees, as this causes S waves to be coupled into the first aluminium layer 8. For angles theta greater than 30 degrees, it has been found that the S wave generation is critical, that is S waves are not transmitted by the first layer 8. It has been found that by arranging the source to project the test signal so that the P wave is critical (that is P wave energy is not coupled into the layer of the laminate material on which the test signal is incident) and the S wave is non-critical (that is S wave energy is coupled into the layer of the laminate material on which the test signal is incident), no refraction occurs at the interface between the layer on which the test signal is incident and its adjacent layer, and also at the deeper interfaces in the laminate material.

Figure 3:
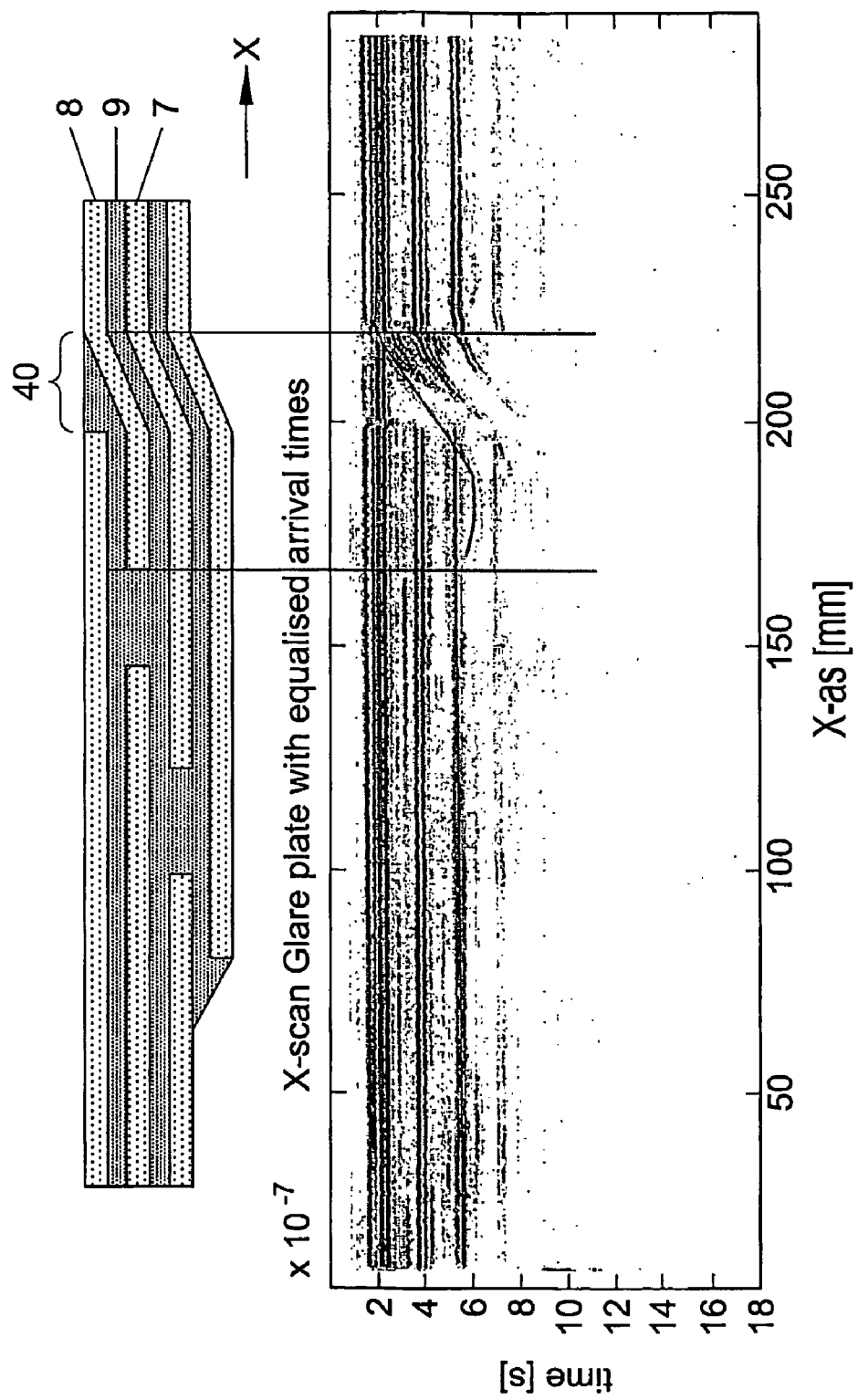
FIG. 3 shows a laminate material having a defect, and the results achieved testing the laminate material according to an embodiment of the present invention.

The coupled test signal thus, comprises both S and P waves. However, preferably, the S wave component S1 predominates. The present invention exploits the insight that the propagation velocity of the S wave S1 in the first layer 8 is approximately the same as the P wave velocity of the P wave component P2 in the second epoxy layer 9. It has been found that the velocity of propagation of S waves in metals, such as aluminium, is of the same order of magnitude as the velocity of propagation of P waves in the non-metal layers of laminate materials, such as metal/epoxy based laminates. Since the velocity of the S wave in the first layer is approximately the same as the P wave in the second layer the conversion of the S wave energy in the first layer to the P wave energy in the second layer is efficient. It will be understood that the closer the velocity match between the first and second layer, the more efficient the conversion of S wave energy to P wave energy will be. Consequently, when the S wave component in the first layer 8 impinges on the second layer 9 not only is the predominant S wave component S1 efficiently converted into a corresponding P wave component P2 in the second layer 9, but because their velocities are approximately the same, no refraction occurs at the interface 10 between adjacent first and second layers 8, 9. However, there are reflections at each interface 10. Hence, the material appears to be homogeneous to the receiver 3. For example, the test signal reflected at the location 2 on the surface of the laminate is reflected to offset O1. The test signal components I1 reflected by the first interface 10 between the first layer 8 and the second layer 9 are reflected to offset O2. Similarly, the test signal components I2 reflected by the second interface 13 between the second layer 9 and a further layer are reflected to a further offset. It will be understood that any defect in the laminate material produce abnormal reflections to those of a defect free interface. Further, a complex structure, for example as shown in FIG. 3 will produce reflections which differ from those produced by a regular structure. Such defects or complex structures will cause reflections to occur at angles which differ from those reflections from defect free or regular structures. These different angles are detected according to an embodiment of the present invention, by the provision of a receiving transducer having a sufficiently large opening angle. Because the test material appears homogeneous to the receiver due to the lack of refraction at the interfaces 10, 13, no further processing of the data obtained by the receiver from the reflected test signal is necessary, in order to obtain a structural image of the test material, refer further to FIG. 3. In addition, FIG. 1 shows details of the apparatus for enabling detection to take place at a plurality of offsets. This is one way of achieving a sufficiently large opening angle. In particular, the source 3 is mounted on a static holder 20 which is fixed with respect to the receiver 5. Although, the holder 20 is referred to as static, it will be understood that it may be moved in order to provide a test signal at a second location. The receiver 3 is mounted on a dynamic holder which is arranged to hold the receiver so that it may be positioned at a plurality of detection locations (also referred to as offsets). Both holders are mounted on a carrier 24. It will be noted that, in contrast to conventional reflective acoustic testing apparatuses, the present invention comprises a plurality of transducers: a transmitting transducer 1 and a receiving transducer 3. Also provided on the carrier 24 is a coupling in order to couple movement from a DC motor 29 to the dynamic holder 22. The DC motor 29 and the coupling 26 are mounted on a mounting block 28. In this way, according to an embodiment of the present invention, measurements may be made at a plurality of locations (in other words at a plurality of offsets), in order to thus identify the depth in the laminate material of any defects. By detecting reflections at a plurality of locations (offsets) any structural features in the laminate material, especially defects, will be more accurately imaged that conventional techniques. In particular, a defect will cause the test signal to be reflected at an angle depending on the nature of the defect, which may cause the test signal to be reflected to a location further from the transmitter in the acquisition plane than would be expected from a defect free laminate. By being able to displace the receiver 3 to a plurality of locations in the acquisition plane reflections from a greater variety of defects are obtained.

In one embodiment, the receiver 3 is scanned along the acquisition plane where data from a plurality of locations is acquired. Alternatively, a plurality of receivers are provided in the acquisition plane in a phased array, and may be further arranged to simultaneously acquire data from the plurality of respective locations at which they are disposed.

In a further preferred embodiment, the receiving transducers have an opening angle of a few degrees, which corresponds to an aperture of less than 20 wavelengths. In contrast to conventional transducers (which typically have an aperture of about 40 wavelengths or more), this preferred embodiment allows reflected test signals from a greater range of reflected angles to be received by the same receiver. This further increases the accuracy with which structural features in the laminate can be imaged. In an alternative embodiment, a large opening angle is achieved by mounting transducer 3 on a support 45 in a rotatable manner so that it is rotatable about a point 45, so as to increase the angular range over which signals generated in the test zone can be detected.

It has been found, for example, that the propagation velocity of an S wave in a metal such as aluminium is of the order of 3000 m/s. Similarly, the propagation velocity of a P wave in an epoxy based layer is 2500-3000 m/s. It is seen that it is not necessary that the velocities match exactly. Indeed, it is seen that in spite of a relatively large discrepancy of for example, 500 m/s, the present invention provides advantageous effects in terms of the accuracy with which structural features are detected and in terms of the direct visibility of the structural features in the reflected data acquired by the receiver or receivers.

In a further embodiment, the laminate material comprises a first epoxy based layer and a second silicon rubber based layer. In this particular embodiment, the S wave in the first epoxy based layer propagates at approximately 1400 m/s and the P wave in the second silicon rubber based layer propagates at approximately 1400-1500 m/s. In this embodiment, it has been found that the present invention similarly works over a range of velocities having a discrepancy of a few 100 m/s, without any discrepancies, such as discontinuities, in the detected data being observed.

Figure 2:
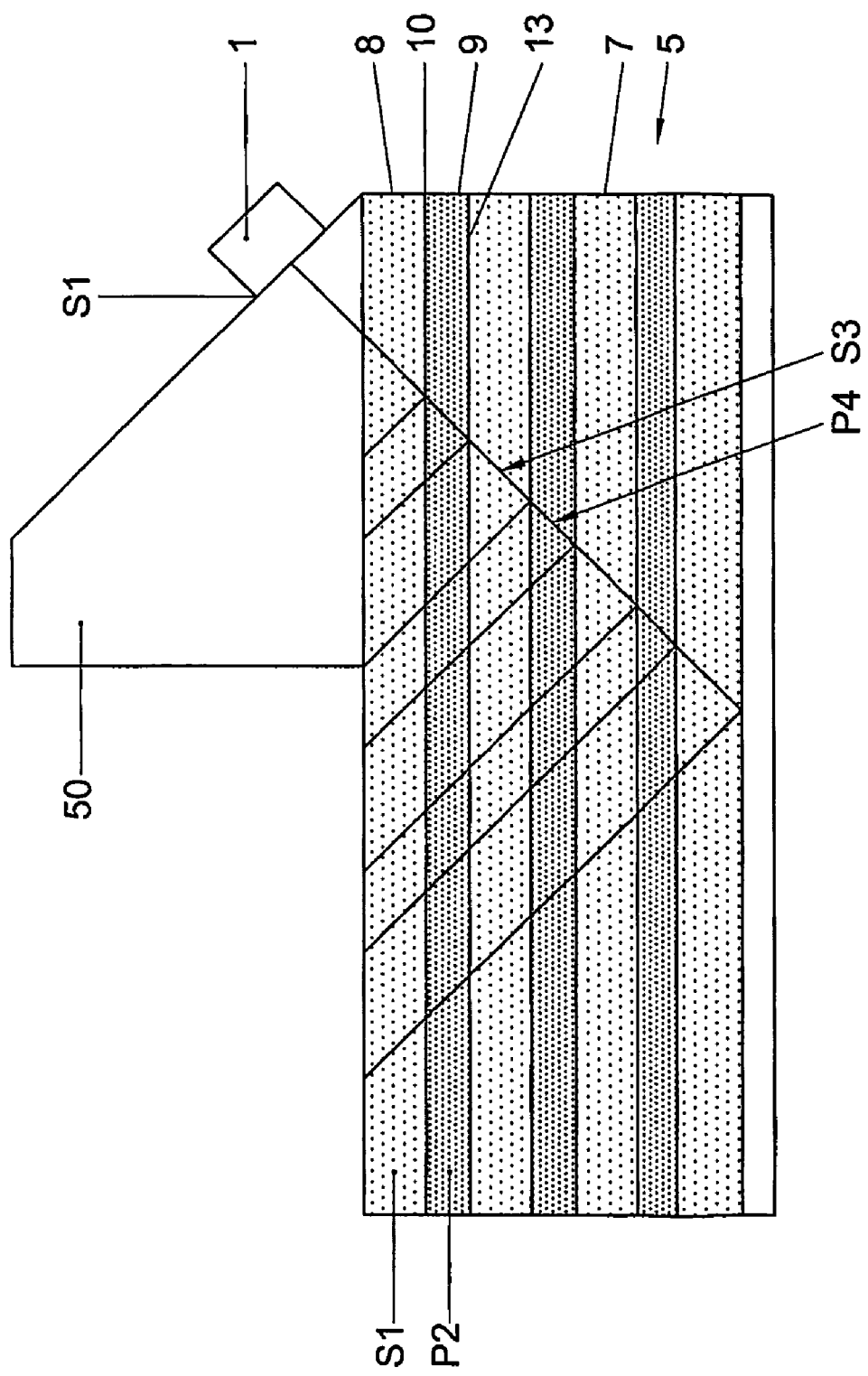
FIG. 2 shows diagrammatically details of an acoustic testing apparatus according to a further embodiment of the present invention.

FIG. 2 shows diagrammatically details of an acoustic testing apparatus according to a further embodiment of the present invention. In FIG. 2 those features having the same reference numbers as features shown in FIG. 1 are the same as those in FIG. 1 and are not described again with reference to FIG. 2, except where they differ. In it has been found that predominantly S waves can be introduced into the first layer by using a transducers which is adapted to generate predominantly S waves. Alternatively, or in combination with such an adapted transducer, a solid element 50 is provided through which the vibrations produced by the transducer are transmitted. It has been found that a solid element 50 improves the coupling of the vibrations in to the laminate material. The solid element may be of any solid material that transmits the vibrations, such as a metal, or plastic. In one embodiment, the transducer is disposed on a surface 51 of the solid element. The surface 51 of the solid element 50 is shaped so that when the transducer is disposed on the surface 51 the vibrations from the transducer are incident on the surface of the laminate at a predetermined desired angle. For example, it may be a wedge shape where the transducer is disposed on a surface 51 which is at an angle to the surface of the laminate. Thus, it is seen that the function of the solid element is two fold: it determines the angle of incidence of the vibrations and it increases the coupling efficiency of vibrations into the test material.

FIG. 3 shows diagrammatically details of an acoustic testing apparatus according to a further embodiment of the present invention. In particular, FIG. 3 shows a laminate material having a complex structure for testing, and the results achieved testing the laminate material according to an embodiment of the present invention. As can be seen the laminate material 7 including a feature (which may also be a defect) 40 which extends through the first four layers of the material including the first and second layers 8, 9. As can be seen from the graph below showing the detected results for the laminate shown in FIG. 2, wherein time is plotted against distance in the x direction, the structural features 40 are directly visible in the data. It is seen that both P and S waves are generated in the first aluminium layer 8. The indicated reflection from the left of FIG. 3 is the desired S wave reflection from the base of the first aluminium layer 8. The reflection in between the top reflection and the S wave base reflection is a P wave. It will be appreciated that in a further embodiment, where predominantly or alternatively only S wave energy is introduced into the first layer, further optimisation is achieved.

A further benefit of the present invention is that time to depth conversion of the data is simple, for example by multiplication by a scalar, since the following equation applies:

$z = t*\cos(theta)*Cs/2$, where z is the depth in the laminate material, t is the time, theta is the angle of incidence and Cs is the velocity of the wave propagation in the laminate.

As described above, it has been found that predominantly S waves are introduced into the first layer by using a transducer and/or using a plastic wedge (rather than water) as the coupling material. As can be see from the graph in FIG. 3, it is not essential that only or predominantly S waves be introduced into the first layer in order to be able to directly observe structural features in the laminate. However, it will be understood that if a significant P-wave component is introduced into the layer on which the test signal is incident, further data processing to remove the P wave component may be necessary. It is further commented that the depth of the structural features is directly obtainable by exploiting the time data on the Y axis of the graph shown in FIG. 3, as described above.

In a further embodiment of the present invention, the data received by the second transducer or transducers is subject to data processing techniques. For example, the data may be subject to a data processing technique to remove internal multiple reflections caused in the test material. One such technique which may be applied, but which is conventionally applied in seismic analysis is Surface Related Multiple Elimination (SRME).

Whilst specific embodiments of the invention have been described above, it will be appreciated that the invention may be practiced otherwise than as described. The description is not intended to limit the invention.

The invention claimed is:

1. An acoustic testing apparatus for testing a laminate material comprising at least one first layer of a first material having a first velocity for a first vibration mode and at least one second layer, adjacent to said first layer, of a second material having a second velocity for a second vibration mode, approximately equal to said first velocity, said acoustic testing apparatus comprising:
   a first transducer for projecting an acoustic test signal onto a first layer of said at least one first layer of a first material disposed in a testing zone; and
   a second transducer for receiving said test signal from said testing zone, and in that said first transducer is adapted to project said test signal at an angle so as to generate vibrations of at least said first vibration mode in said first layer, wherein said vibrations of said first vibration mode are incident on an interface with said second layer of said second material under an incidence angle so as to produce vibrations of at least said second vibration mode in said second layer, so that refraction of said test signal at said interface is suppressed.

2. An acoustic testing apparatus according to claim 1, wherein said first transducer is adapted to project said test signal at an angle so that said vibrations of said first vibration mode predominate in said first layer.

3. An acoustic testing apparatus according to claim 1, wherein said first transducer is adapted to project said test signal at an angle so as to suppress in said first layer the generation of vibrations of at least said second vibration mode.

4. An acoustic testing apparatus according to claim 1 wherein said second transducer is arranged to receiving said test signal reflected from said testing zone.

5. An acoustic testing apparatus according to claim 1, wherein said second transducer is adapted to receive said reflected test signal at one or more locations.

6. An acoustic testing apparatus according to claim 1, wherein data associated with said laminate material is directly derivable as a function of time and position from said reflected test signal received by said second transducer.

7. An acoustic testing apparatus according to claim 6, wherein said angle corresponds to the angle of incidence of said test signal on said first layer measured with respect to the normal, and is between approximately 14 and 30 degrees.

8. An acoustic testing apparatus according to claim 1, wherein at said interface said vibrations of said first vibration mode are converted to vibrations of said second vibration mode.

9. An acoustic testing apparatus according to claim 1, said vibrations of said first vibration mode are a shear wave and said vibrations of said second vibration mode are a compression wave, or vice versa.

10. An acoustic testing apparatus according to claim 1, wherein the frequency of said test signal is in excess of the order of 20 MHz.

11. An acoustic testing apparatus according to claim 1, further comprising a plurality of second transducers arranged in an array.

12. An acoustic testing apparatus according to claim 1, wherein said second transducer is arranged to be moveable to a plurality of locations for receiving said reflected test signal.

13. An acoustic testing apparatus according to claim 1, wherein said second transducer is rotatably mounted on a support.

14. An acoustic testing apparatus according to claim 1, wherein said first transducer is disposed on a surface of a solid element, wherein said surface is arranged so as to cause said first transducer to project said vibrations at said incidence angle.

15. An acoustic testing method for testing a laminate material comprising at least one first layer of a first material having a first velocity for a first vibration mode and at least one second layer, adjacent so said first layer, of a second material having a second velocity for a second vibration mode, approximately equal to said first velocity, said acoustic testing method including the steps of:
   using a first transducer to project an acoustic test signal onto a first layer of said at least one first layer of a first material disposed in a testing zone; and
   using a second transducer to receive said test signal reflected from said testing zone, and by adapting said first transducer to project said test signal at an angle so as to generate vibrations of at least said first vibration mode in said first layer, wherein said vibrations of said first vibration mode are incident on an interface with said second layer of said second material under an incidence angle so as to produce vibrations of at least said second vibration mode in said second layer, so that refraction of said test signal at said interface is suppressed.

* * * * *